US 6,315,740 B1

(12) United States Patent
Singh

(10) Patent No.: US 6,315,740 B1
(45) Date of Patent: Nov. 13, 2001

(54) SEIZURE AND MOVEMENT MONITORING APPARATUS

(76) Inventor: Balbir Singh, 15902 Maplehurst Dr., Spring, TX (US) 77379

( * ) Notice: Subject to any disclaimer, the term of this patent is extended or adjusted under 35 U.S.C. 154(b) by 0 days.

(21) Appl. No.: 09/389,695

(22) Filed: Sep. 4, 1999

Related U.S. Application Data

(60) Provisional application No. 60/134,465, filed on May 17, 1999.

(51) Int. Cl.[7] ............................. A61B 5/103; A61B 5/117
(52) U.S. Cl. ........................................................ 600/595
(58) Field of Search .................................. 600/595, 552, 600/510, 553, 587; 340/573

(56) References Cited

U.S. PATENT DOCUMENTS

| | | |
|---|---|---|
| 4,197,856 | 4/1980 | Northrop . |
| 4,320,766 | 3/1982 | Alihanka et al. . |
| 5,194,847 | 3/1993 | Taylor et al. . |
| 5,523,742 * | 6/1996 | Simkins et al. ................... 340/573 |
| 5,610,590 * | 3/1997 | Johnson et al. .................. 340/573 |
| 5,808,552 * | 9/1998 | Wiley et al. ....................... 600/595 |
| 5,879,309 * | 3/1999 | Johnson et al. .................. 600/552 |
| 5,905,436 * | 5/1999 | Dwight et al. .................... 600/595 |

FOREIGN PATENT DOCUMENTS

WO 96/36950  11/1996  (WO) .
WO 98/34577  8/1998  (WO) .

* cited by examiner

*Primary Examiner*—John P. Lacyk
*Assistant Examiner*—Brian Szmal
(74) *Attorney, Agent, or Firm*—Trop, Pruner & Hu, P.C.

(57) ABSTRACT

An apparatus for accurately monitoring motor movements attributable to seizures and convulsions of patients having epilepsy or other seizure disorders, and motor movements attributable to periodic leg movements, tremors, respiration, mechanical cardiac functions, or any other motorics during periods of sleep. This monitoring function is achieved without attaching any detection apparatus to the patient. Embodiments measure patient movements essentially by relating mattress displacement to such motor movements. The preferred embodiment is constructed with a geophone configuration intended to receive an analog signal corresponding to mattress movement and to communicate this signal to an electrically interconnected detection assembly for monitoring and recording the patient's pattern of body movements. Other suitable movement sensing devices such as devices based upon piezoelectric, fiber optics, microwave, infrared, and ultrasound phenomena may be used either in addition to or instead of geophones. The analog signals received by these sensors are then communicated to a computerized detection assembly wherein these signals are converted from waveforms to digital signals for subsequent analysis and remedial medical treatment as appropriate.

45 Claims, 5 Drawing Sheets

I Hour

I Hour

I Hour

II Hour

III Hour

20 Seconds

SEIZURE AND MOVEMENT MONITORING APPARATUS

RELATED APPLICATIONS

This application claims priority based upon Provisional U.S. application Ser. No. 60/134,465 filed May 17, 1999.

BACKGROUND OF THE INVENTION

This invention relates to seizure monitors, and more particularly relates to means for monitoring movements attributable to seizures and convulsions of patients having epilepsy or other seizure disorders.

As is well known by those skilled in the art, it is common practice to attach electrodes to patients to observe bio-electrical body functions. For instance, electrical activity of the heart may be monitored by electrodes interconnected with the body. Unfortunately, electrodes are inconvenient and tend to become detached from the patient, wherein false alarms and patient-anxiety are undesirable sideeffects. Furthermore, if and when, a patient awakes while being observed and monitored, electrodes are likely to result in physical and psychological discomfort, and inhibited mobility. Such adverse reactions to monitoring devices are obviously contrary to efforts to remedy and improve a patient's infirmity and to improve a patient's well-being.

In U.S. Pat. No. 4,320,766, Alihanka et al. attempt to improve the art with a "static charge sensitive bed" that records signals corresponding to a patient's body movements while disposed in a supine position in bed. Configured with an antenna assembly to communicate amplified signals for recording changes in static charges produced by body movements, this bed may be used to monitor a patient's motor activity during sleep. Instead of using electrodes or the like, the Alihanka bed is constructed with a built-in antenna assembly consisting of plates, nets, or rods arranged in a matrix contained in a supplemental mattress disposed either between the patient and the regular mattress or beneath the regular mattress. However this assembly is complicated and somewhat cumbersome to apply to patients, and to operate without inadvertent interference by patients.

Notwithstanding these and related developments in the art, there appears to be no apparatus which provides a means for providing accurate, reliable, and interference-free signals corresponding to the motor movements of patients experiencing seizures, convulsions, and other sleep disorders during periods of sleep.

Accordingly, these limitations and disadvantages of the prior art are overcome with the present invention, wherein a seizure monitoring apparatus is provided that is particularly useful for enabling accurate and unobtrusive monitoring and recording of movements attributable to seizures and convulsions of patients having epilepsy or other seizure disorders.

SUMMARY OF THE INVENTION

The present invention provides an apparatus for accurately monitoring a patient's body movements during periods of sleep. In particular, the present invention monitors motor movements attributable to seizures and convulsions of patients having epilepsy or other seizure disorders, and motor movements attributable to periodic leg movements, tremors, respiration, mechanical cardiac functions, or any other motorics during periods of sleep. As will be hereinafter described, the present invention achieves this monitoring function without attaching any detection apparatus to the patient. Embodiments of the present invention measure patient movements essentially by relating mattress displacement to such motor movements. In order to reliably and accurately monitor such movements, it has been found that accurate sensing devices such as geophones—representative of seismic sensors or velocity sensors—or the like should preferably be used.

The preferred embodiment of the present invention is constructed with a geophone configuration intended to receive an analog signal corresponding to mattress movement and to communicate this signal to an electrically interconnected detection assembly for monitoring and recording the patient's pattern of body movements. According to the preferred embodiment, a plurality of insulated and padded geophones is parked upon a bed proximal to a patient situated thereon in a supine position. These geophones may alternatively be attached to the head-board, side-rail or the foot board of the bed. Any patient body movements cause corresponding displacements in the underlying mattress and the bed-frame that are, consequently, received by the plurality of geophones or the like. It will be appreciated that the present invention also contemplates that other suitable movement sensing devices such as devices based upon piezoelectric, fiber optics, microwave, infrared, and ultrasound phenomena may be used either in addition to or instead of geophones, so long as the sensitivity contemplated by the present invention is obtained. As will be appreciated by those skilled in the art, to achieve the objectives of the present invention, such sensors may require positioning on the bed or, in case of microwave, infrared, and ultrasound motion sensors, may require hanging positioning from a wall near the bed or from the ceiling thereabove.

The analog signals received by these sensors are then communicated to a computerized detection assembly wherein these signals are converted from waveforms to digital signals for subsequent analysis and remedial medical treatment as appropriate. Once these digital signals are analyzed, if seizures or convulsions or other sleep disorders appear to be occurring, then medical professionals or other healthcare personnel, including family members, are notified either locally or remotely.

It is an object of the present invention to provide an apparatus for accurately monitoring a patient's body movements during periods of sleep.

It is still another object of the present invention to provide an apparatus for promoting the safety and health of patients suffering from epilepsy, seizures, and other sleep disorders.

It is yet another object of the present invention to provide an apparatus that detects most patients' motor seizures during periods of sleep.

It is yet another object of the present invention to provide an apparatus that detects some patients' complex partial motor seizures during periods of sleep.

It is still another object of the present invention to provide an apparatus that detects patients' motor movements attributable to epileptic convulsive seizures and other deviant movements including periodic leg movements, tremors, respiration, mechanical cardiac functions, or any other motorics during periods of sleep, without attaching any detection apparatus to the patient.

These and other objects and features of the present invention will become apparent from the following detailed description, wherein reference is made to the figures in the accompanying drawings.

IN THE DRAWINGS

DETAILED DESCRIPTION

Figure 1:
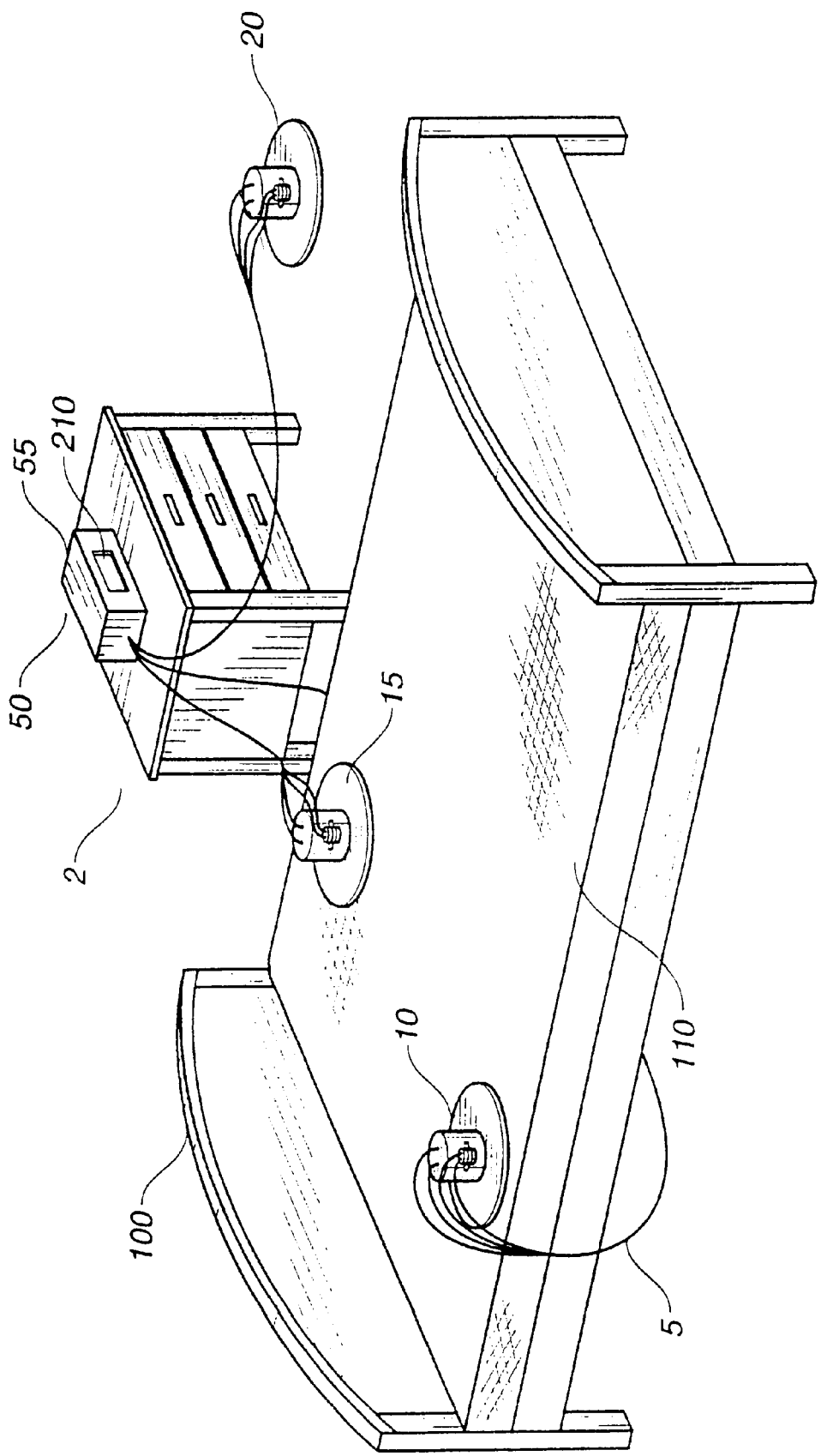
FIG. 1 depicts a simplified frontal perspective view of a preferred embodiment of the present invention.

Now referring to FIG. 1, there is shown a simplified perspective view of the preferred embodiment of the present invention 2 comprising plurality of sensing means 5 disposed upon mattress 110 and adjacent or proximal to bed 100. Plurality of geophone sensing means 5 is electrically interconnected with detection assembly SO. As will be appreciated by those skilled in the art, according to the present invention, a patient is sleeping upon mattress 110 with geophones 10 and 15 of plurality of geophones 5 disposed upon the mattress adjacent or proximal to the patient. As patient body movements occur during sleep, corresponding displacements of mattress 110 occur. These displacements are communicated to at least one of geophones 10 and 15, which, in turn, communicate these signals to detection apparatus 50 within its housing 55 as will be hereinafter described in detail.

Geophone 20 is preferably disposed proximal to bed, e.g., on the floor, to establish a baseline or reference for signals that are attributable to environmental conditions, i.e., that are extraneous to the patient. Such environmental conditions may include vibrations from walking or from nearby elevators or escalators, vehicular traffic, etc. It will be understood by those skilled in the art that patient movements will always generate stronger signals in geophones 10 and 15, placed upon the mattress, compared to geophone 20, placed on the floor or on a structure away from the bed. It will be appreciated that the sensitivity of the plurality of geophones may be changed in order to obtain optimal results. It will also be understood that a plurality of sensors may also be used, if necessary, to properly monitor vibrations attributable to environmental conditions extraneous to a patient's body movements.

Figure 2:
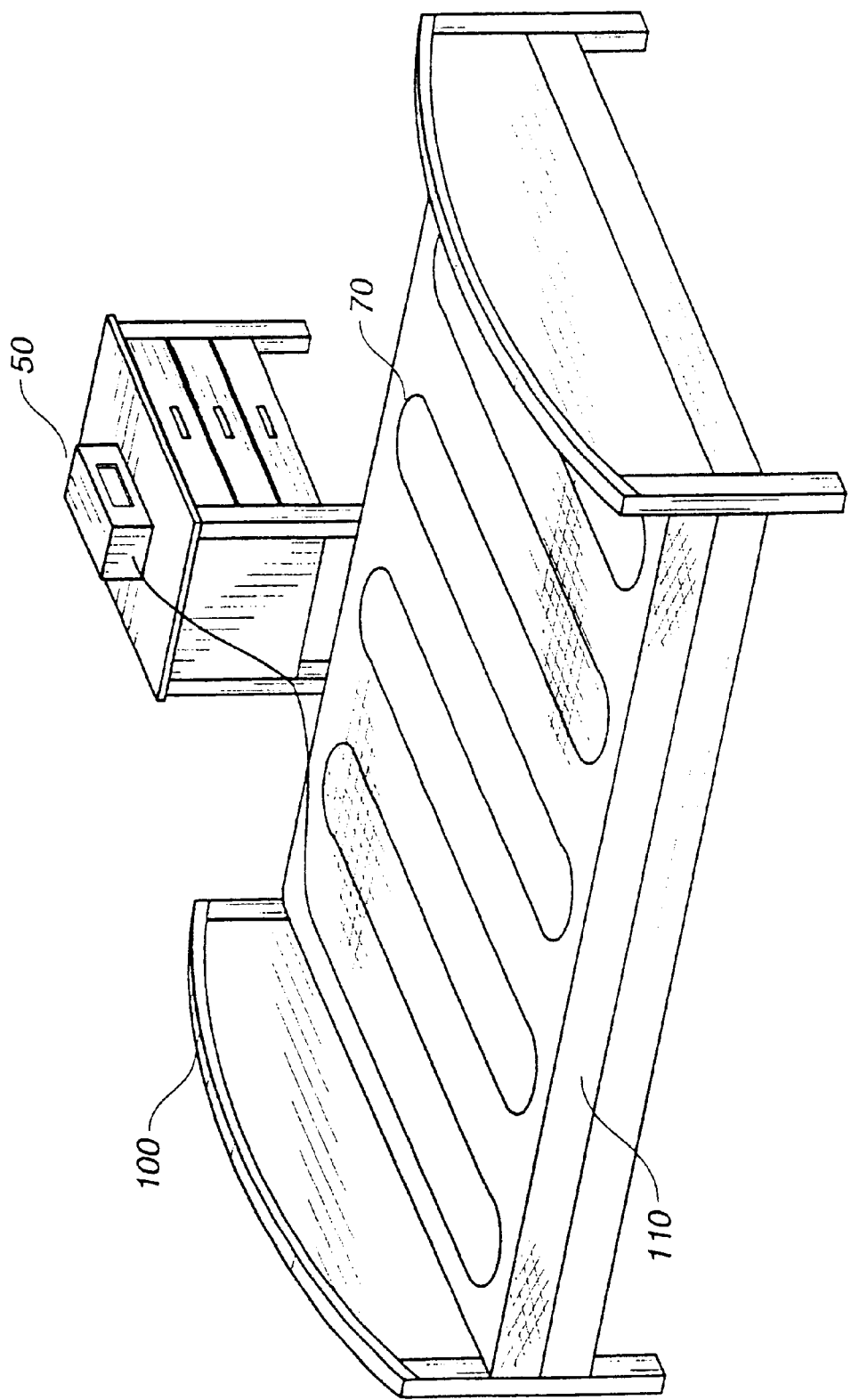
FIG. 2 depicts a simplified frontal perspective view of an alternative embodiment of the present invention.

Another embodiment of the present invention is depicted in FIG. 2, wherein instead of a plurality of geophones to sense a patient's motor movements during sleep, a plurality of fiber optics sensors 70 is used. U.S. Pat. No. 5,194,847 generally describes the benefits and applicability of fiber optics for sensing movements and the like. According to the present invention, plurality of fiber optics sensors 70 should preferably be disposed in a sheet-like layer that may be conveniently snugly placed immediately above the mattress cover obviously disposed around mattress 110 or, alternatively, disposed immediately beneath the top sheet.

Figure 3:
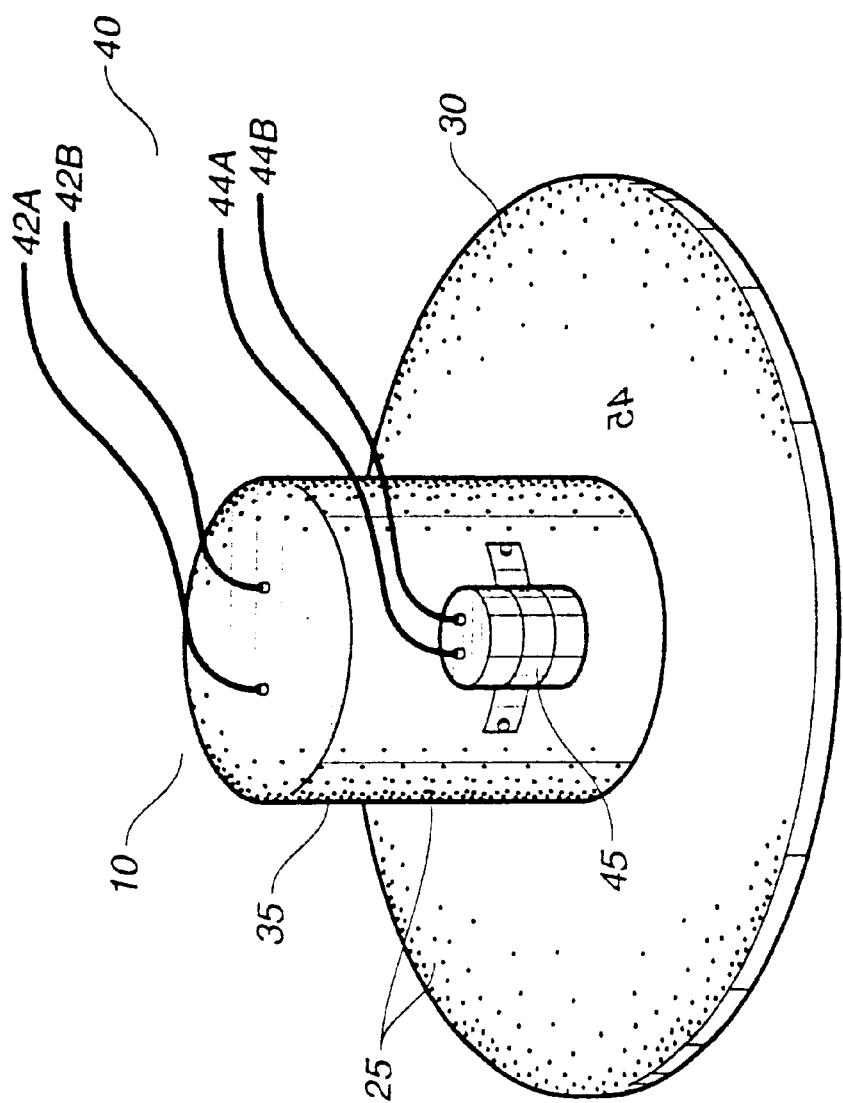
FIG. 3 depicts an isolated frontal view of a portion of the preferred embodiment depicted in FIG. 1.

Now referring to FIG. 3, there is seen an isolated perspective view of a typical geophone contemplated by the embodiment depicted in FIG. 1. A commonly used geophone contemplated under the present invention consists of a magnetic device that detects movements. Using a suspended magnet, the geophone, upon movements occurring in its proximity, produce a proportional voltage (preferably measured in millivolts) through its winding. As will be understood by those skilled in the art, the amplitude of the output voltage is proportional to the intensity of the movement detected. Core-less DC motor member 45, akin to the motor incorporated into commonly used pager-vibrators, is typically affixed atop the sensor's housing. This motor is turned on periodically to test the functionality of the geophone and detection system.

Thus, in FIG. 3, geophone 10 is shown having housing 35 and mounted upon base plate 30. Since, as is known by those skilled in the art, geophones occasionally fail to properly obtain signals, vibrator motor member 45 is used to assure proper operation of geophone 10. By periodically activating vibrator member 45, a small movement is engendered in geophone 10. If the signal conditioning circuit 120 fails to receive a response from the geophone under these artificial, test circumstances, then a warning alarm or the like is preferably generated, alerting the operator that a geophone malfunction has occurred.

Geophone 10 is preferably adapted to include cushion means 25 the surrounding housing 35 and base plate 30, functioning as both electrical insulation and as a physical barrier to prevent patient discomfort should inadvertent contact therewith occur.

Other aspects of the computer system contemplated by the present invention include an LED light 220 to indicate if the system is operational. In the preferred embodiment, the LED light should blink whenever the trigger threshold is exceeded: in FIG. 1, this condition corresponds to the amplitude of the waveform generated from each geophones 10 and 15 disposed on the patient's bed being higher than the amplitude of the waveform generated from geophone 20 disposed on the floor. On the other hand, the LED light should remain illuminated once an alarm condition has been met, or under a malfunction-situation When a malfunction or a real alarm situation occurs, LCD 210 should display the nature of the malfunction or the alarm condition.

Since the alarm aspect of the present invention is inherent in the integrity and reliability of the monitoring function, to prevent accidental alarm-deactivation, the process of silencing an alarm should preferably require sequential pressing of two keys. According to the teachings of the preferred embodiment of the present invention, even after an alarm is deactivated, the LED should stay on until another, confirming sequence of keys is pressed. It will be understood that, when a malfunction occurs, there should preferably be simultaneous audio alarm and illumination of the LED light. The alarm may, of course, be deactivated as usual, but it should recur every 5 minutes or the like unless the malfunction has been corrected or unless the present invention has been switched off presumably because more than just immediate remedial action is needed for normal operation. It should be understood, of course, that if a system malfunction has occurred, the malfunction alarm or equivalent signal means should be readily distinguishable from a warning tone or other signal means, and the LED display will indicate that a malfunction or the like has occurred.

Additionally, it is contemplated that switching-off embodiments of the present invention should also preferably consist of a two step process. Thus, the turn-off keys should be programmed such that the sequential keys are not close to each other. It has been found that providing backup battery for power failure up to 12 hours long is advantageous for uninterrupted monitoring of patients' sleep even under conditions of adverse weather and the like. The present invention also provides circuit protection well known in the art for the patient during monitoring, thereby preventing any 115V current from being communicated to a geophone situated on the patient's bed. Software of the present invention should preferably be programmed to pick up sustained seizures lasting for more than a preset length of time and a preset number of short but frequent seizures. Those skilled in the art will, of course, understand that, generally, the various settings prerequisite for accommodating the present invention to a patient's needs and specific seizure-type are programmable in software, ROM, or the like, in a manner known in the art. Thus, the duration of a patient's seizure and the frequency thereof prerequisite to triggering an alarm condition depends upon the patient's particular needs. Such patient-parameters will, of course, be input to the present invention as hereinbefore described for proper monitoring of the patient's seizures and the like.

It has been found that blanketing an embodiment of the sensing apparatus of the present invention with suitable padding 25 is preferable for the patient's comfort. As hereinbefore described, the plurality of geophones 5 or the like that detect patient movements may be either placed on a patient's bed or disposed on the bed side-rail or even affixed to the head-board or foot-board. Plurality of wires 40 interconnect geophone 10 with detection assembly 50 (FIG. 1). More particularly, pair of wires 42 A, B interconnect the geophone circuitry with the detection circuitry while pair of wires 44 A, B interconnect vibrator 45 with detection circuitry.

Figure 4:
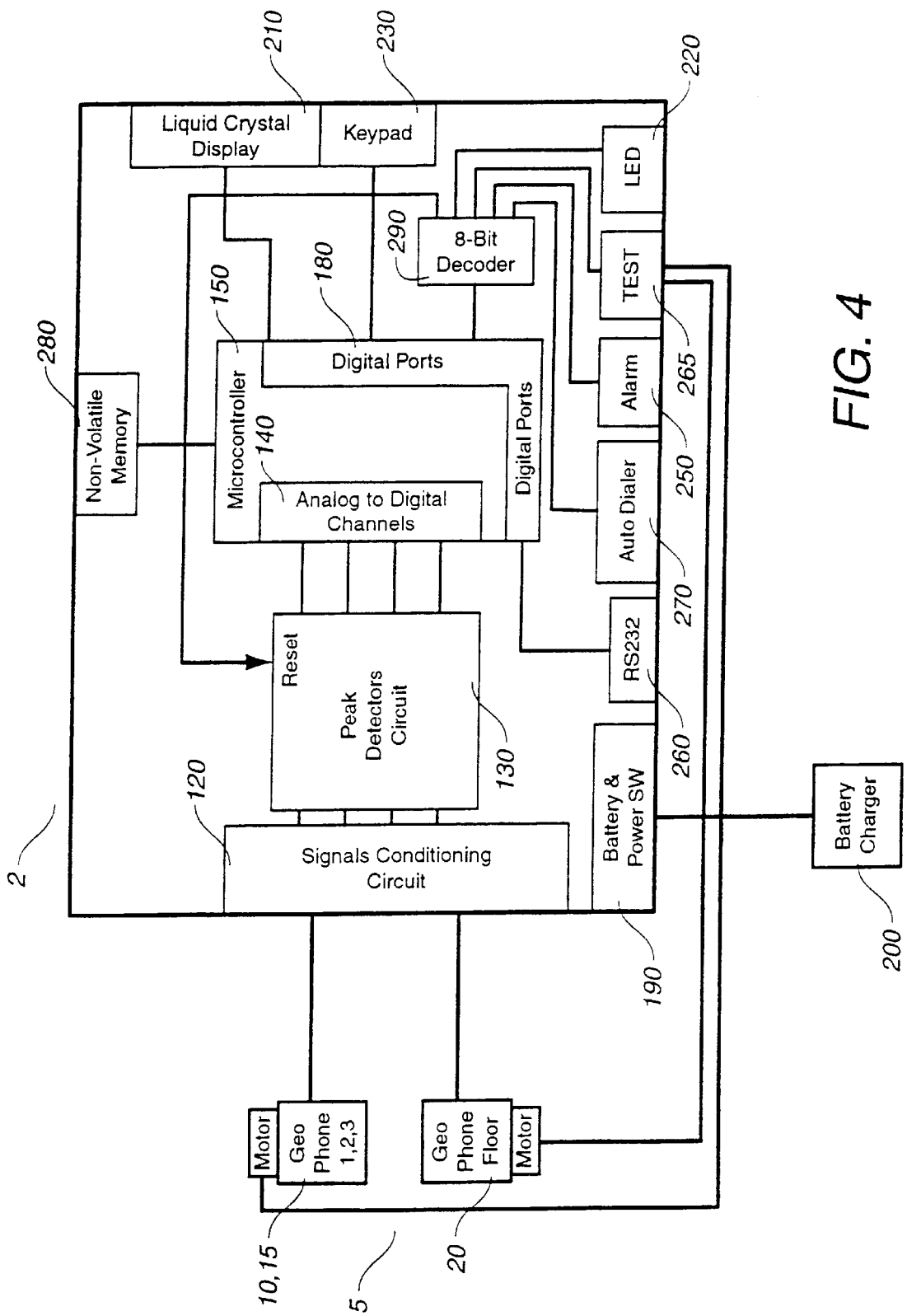
FIG. 4 depicts a simplified schematic block diagram of the preferred embodiment depicted in FIG. 1.

Referring now to FIG. 4, there is shown a simplified schematic in block diagram form of the detection and analysis circuitry 50 comprising the preferred embodiment of the present invention 2 depicted in FIG. 1. By comparing the cumulative analog signals received by plurality of geophones 10 and 15 disposed upon mattress 110 or alternatively received by various other types of motion sensors known in the art, or a combination thereof, and the base line signal received by geophone 20 disposed upon the floor or the like, the incidences of motor movements engendered by a sleeping patient may be continuously monitored by conditioning circuit 120.

In a manner well known in the art, this conditioning circuit uses filters and other components to amplify or attenuate the waveform incoming from the plurality of geophones 5 to a sufficient amplitude that may be input to the peak detectors circuit 130 that counts the peaks every second. Ergo, the geophones' signals are terminated and then amplified to 0–2.5 V full-scale signals. These conditioned signals are calibrated such that the voltage conditioned from each geophone is equal to the same intensity of the movement at each geophone. It should be clear that peak detecting via circuit 130 is used to measure the highest voltage generated at each geophone. This detection is preferably performed every second to measure the highest intensity of the movement every interval (second). According to the preferred embodiment, this peak is reset by software every second. A low-pass filter is included in peak detectors circuit 130 to filter any 50–60 Hz power noise from the input signals.

The peak voltages that are preferably detected each second are then read through analog-to-digital converter 140. These analog signals are converted to a digital signal, e.g., an eight-bit digital byte, representing the peak intensity that is proportional to the highest movement intensity during the 1-second interval. As will be understood by those skilled in the art, a microcontroller or microprocessor 150 is preferably used to perform a plurality of tasks as will be hereinafter described. Upon power up, microcontroller/microprocessor 150 executes a conventional start-up sequence. In particular, microcontroller/microprocessor 150 resets all the circuitry depicted in FIG. 4, and fetches the firmware from its non-volatile memory. It next interfaces with the user through keypad 230 and liquid crystal display ("LCD") 210 to set the intervals, movement intensity threshold, number of movement episodes to constitute an alarm condition, number of repeated movements in sequence to trigger alarm 250, and to set the operating mode to monitor, idle, and setup modes.

As hereinbefore described, microcontroller/microprocessor 150 coordinates the determination of whether detected movements are due to extrinsic causes. By comparing the signal level of geophones 10 or 15 with the reference level from floor geophone 20, this determination is readily made. If only the floor movement is detected then, of course, the signal generated is deemed to be extraneous and is consequently ignored. As will be appreciated by those skilled in the art, suitable software or the like enables the three peak detected signals to be read from the plurality of geophones preferably disposed on the bed. The peak with the highest intensity is compared with the preset threshold value. If the movement is above the set intensity, then LED 220 is caused to blink, thereby indicating that a patient's movement has been detected.

Detected patient movements are recorded preferably in a non-volatile memory 280 for a period of up to twelve hours. As will be evident to those skilled in the art, the collected data may then be downloaded to a PC via RS232 port 260. RS232, of course, is an industry standard for serial asynchronous communications in which the signal is switched from +9V to −9V as Mark Signal. Microcontroller/microprocessor 150 communicates externally of the circuit of the present invention through input/output digital ports 180. Numeral 290 represents an 8-bit addressable latch 1-of-8 decoder. Due to the limited number of digital I/O lines on microcontroller/microprocessor 150, latch decoder means 290 is used to read a specific address code from the I/O port which, of course, corresponds to an address of an output device such as autodialer 270, alarm 250, LED 220, and test motor 265. Autodialer 270 comprises a contact switch well known in the art for activating an external autodialer device. In a manner well known in the art, a bit is set on Low or High to either reset or set the corresponding device.

Keypad 230 is provided for setting the time interval and period as contemplated by the present invention. By making a suitable keypad-based request to the operational software, the recorded time of a patient's motor movement may be displayed. A liquid crystal display 210 or the like is provided to display pertinent alphanumeric information indicative of the status of the patient's sleep behavior. In a manner well known in the art, Start/Stop switches are provided via a programmed set of preferably two numeric keys to start or stop monitoring a patient's sleep activity. The apparatus contemplated by the present invention is powered via conventional battery charger adapter 200. Adapter 200 preferably comprises a commonly used lead-acid battery charger suited to battery 190, and regulates and charges lead-acid battery 190 from a 120 vac power source. Leadacid battery 190 or the like is used to provide a source of DC power for operation without external power source. It should be evident, however, that any suitable battery and battery charger known in the art may be used to power embodiments of the present invention. Battery 190 is directly connected to adapter 200. A toggle switch connected to the combination of adapter 200 and battery 190 provides a conventional and convenient way to switch off the system. As will be readily appreciated by those skilled in the art, if case power should fail, this battery assures continuous, uninterrupted operation of the apparatus taught by the present invention preferably for up to 12 hours.

If a patient is detected to have experienced a motor movement within an interval, then the time for such movement is recorded preferably in nonvolatile memory. This memory means should preferably have the capacity to store up to twelve hours of data in one-second intervals. If the patient's motor movement continues and exceeds the programmed value, the microprocessor/microprocessor will activate external and visual alarm 250.

Figure 5A:
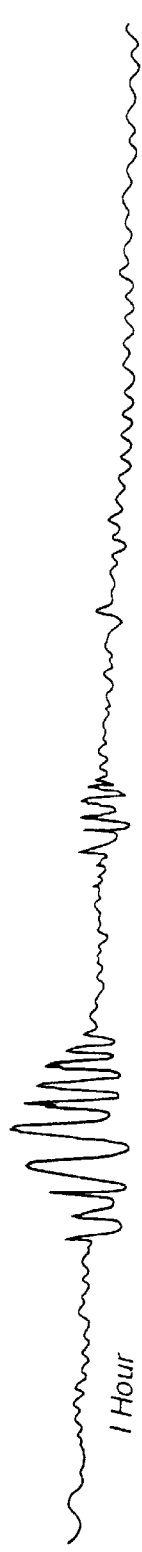
FIG. 5A depicts a waveform representing a patient's normal sleep activity recorded by an embodiment of the present invention.
Figure 5B:
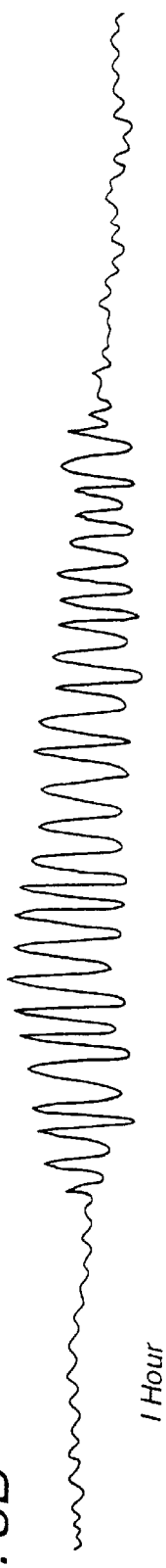
FIG. 5B depicts a waveform representing a patient's 80-second seizure activity recorded by an embodiment of the present invention.
Figure 5C:
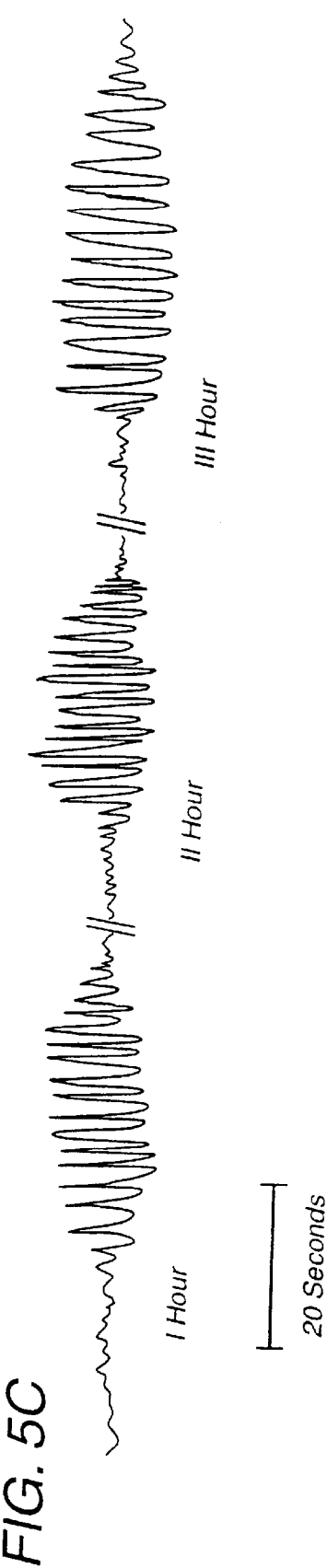
FIG. 5C depicts a waveform representing a patient's series of three 30-second seizures recorded over a three-hour period by an embodiment of the present invention.

Referring now collectively to FIGS. 5 A, B, and C, there is depicted representative waveforms, collected by the plurality of sensors contemplated by the present invention, that are typically analyzed by detection and analysis circuitry 50 as hereinbefore described. More particularly, FIG. 5A shows an illustration of a patient's normal sleep activity. On the other hand, FIG. 5B shows the waveform corresponding to a patient having a seizure approximately 80 seconds in duration. Under the preferred embodiment, such an illustrative waveform should, of course, trigger an alarm indicating that a seizure is occurring. Similarly, FIG. 5C shows an illustrative representation of three smaller seizures of about 30 seconds duration each, spread over a three-hour period.

As will be appreciated by those skilled in the art, as hereinbefore described, the internal computer instructions contemplated by the present invention may be programmed and implemented in software or ROM or the like to accept keyboard input indicating whether such an incidence of small seizure intervals in a particular period should trigger an alarm. Thus, peak detectors of the present invention are driven by the underlying software or the like to detect and measure the peaks. Then, the microcontroller/microprocessor member 150 assess whether a particular series of waveforms are above the amplitude and length threshold; if such waveforms are below the threshold, then no motor movement is considered to have occurred.

It is another feature and advantage of the present invention that the warning alarms and associated display may be communicated either locally or remotely to medical practitioners, healthcare personnel, or family. If the patient does not deactivate a local alarm contained in the present invention, as will happen if the patient is, indeed, having a seizure, then microcontroller/microprocessor 150 will activate a remote alarm in another part of the house or in a nursing station or the like. This alarm may be connected to the monitor apparatus of the present invention with a wire or may comprise a wireless remote alarm controlled with electromagnetic signals or the like. For situations in which no one resides in the same house as a particular patient, the microcontroller/microprocessor of the present invention may be programmed to activate auto-dialer 270 to dial a predetermined telephone number and to play a prerecorded message. As will be evident to those skilled in the art, this telephone number preferably summons a monitoring station or may summon a family member or "911." As should be clear to those skilled in the art, a monitoring station will be able to interact with the microcontroller/microprocessor to deactivate the alarm and also change the monitoring settings, if needed. It should be understood that the duration of a patient's seizure and the frequency thereof that will trigger an alarm condition depends upon the patient's particular needs. Such patient-parameters will, of course, be input to the present invention as hereinbefore described for proper monitoring of the patient's seizures and the like. The auto-dialer function contemplated by the present invention is capable of calling a sequence of telephone numbers until a sequence of keys are pressed at the other end.

For battery operation or battery backup, the conventional combination of battery 190 and battery charger 200 assure an uninterrupted power source if power via normal mains should become unavailable. That is, when a power outage or failure occurs, battery backup automatically takes over as the power source. It will be appreciated that battery charger 200 keeps battery 190 charged at all times. Thus, the apparatus taught by the present invention has access to battery-power at all times. In case of power failure or the like, the battery sustains power to the device for approximately 12 hours, obviously depending upon battery-selection criteria well known in the art.

Thus, the present invention affords an apparatus heretofore unknown in the art wherein geophones and the like are used to afford very sensitive and reliable detection of patients' minute movements for the purpose of monitoring seizures. By processing the clean signals generated by this superior movement detection, the circuitry and software of the present invention provide a means and method for effectively monitoring seizure-caused movements.

It is also within the concept of the present invention that geophones hereinbefore described may be placed upon a patient's bed not only by itself, but also with a plurality of plastic flexible strips that are spread under the bed sheet and connected to each other. Thus, a geophone may be placed atop this arrangement to promote its sensing function. It will be understood that, instead of such strips, suitable wires and the like may be used. As another alternative embodiment of the present invention, a water-filled mattress may be used to inherently promote the sensitivity of sensors to vibrations caused by a patient's motor movements during seizures, convulsions, or other sleep disorders. In this embodiment, one spot on one of the corners of the mattress may be made of low resistance plastic: a geophone may then be placed on this spot to pick up even the smallest vibrations manifest in the water.

It will also be appreciated that the present invention contemplates that other suitable patient-movement sensing devices based upon piezoelectrics, fiber optics, microwaves, infrared, and ultrasound may be used in addition to or instead of geophones. As hereinbefore described, such sensors may either be positioned upon a patient's bed or, particularly in case of microwave, infrared, and ultrasound-based based motion sensors, may be situated from a wall adjacent or the ceiling above the bed.

Other variations and modifications will, of course, become apparent from a consideration of the structures and techniques hereinbefore described and depicted. Accordingly, it should be clearly understood that the present invention is not intended to be limited by the particular features and structures hereinbefore described and depicted in the accompanying drawings, but that the present invention is to be measured by the scope of the appended claims herein.

What is claimed is:

1. A patient movement monitoring device comprising:
   a sensor assembly adapted to be placed proximal to a patient and responsive to movement of the patient; and a detector circuit operatively coupled to the sensor assembly, the detector circuit adapted to detect (1) sustained patient movement of more than a first specified magnitude for more than a first specified time period, and (2) a plurality of patient movement episodes of more than a first specified magnitude and more than a second specified duration, the plurality of patient movement episodes occurring within a third specified time period, and the detector circuit is further adapted to generate an alarm signal indicative of a seizure condition if at least one of the above events is detected, wherein the first specified magnitude and the second specified magnitude are substantially the same.

2. The patient movement monitoring device of claim 1, wherein the third specified time period is longer than the first specified time period and the first specified time period is longer than the second specified time period.

3. The patient movement monitoring device of claim 2, wherein the first specified time period is approximately 60 seconds, the second specified time duration is approximately 30 seconds, and the third specified time period is approximately 3 hours.

4. A patient movement monitoring device comprising:
a sensor assembly adapted to be placed proximal to a patient and responsive to movement of the patient; and
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period,
wherein the sensor assembly is selected from the group consisting of a geophone, fiber optic, microwave, infrared, and ultrasound sensor assemblies.

5. The patient movement monitoring device of claim 4, wherein the sensor assembly is adapted to be placed on a surface on which the patient is located.

6. The patient movement monitoring device of claim 4, wherein the sensor assembly is adapted to be placed in a position capable of detecting motion of the patient.

7. The patient movement monitoring device of claim 1, wherein the alarm signal comprises a visual indication of the seizure condition.

8. The patient movement monitoring device of claim 7, wherein the alarm signal further comprises an audible indicator.

9. The patient movement monitoring device of claim 7, wherein the alarm signal may be cancelled within a fourth specified time period.

10. The patient movement monitoring device of claim 9, wherein the fourth specified time period is approximately 2 minutes.

11. The patient movement monitoring device of claim 9, further comprising a notification device responsive to the alarm signal, the notification device adapted to alert a designated location if the alarm signal is not reset within the fourth specified time period.

12. The patient movement monitoring device of claim 11, wherein the notification device is adapted to contact the designated location through a plain old telephone system.

13. The patient movement monitoring device of claim 12, wherein the notification is adapted to contact the designated location through a radio frequency transmitter.

14. The patient movement monitoring device of claim 13, wherein the radio frequency transmitter comprises a wireless telephone system.

15. The patient movement monitoring device of claim 1, wherein the detector circuit is adapted to receive one or more signals from the sensor assembly every approximately 1 second.

16. A patient movement monitoring device comprising:
a sensor assembly adapted to be placed proximal to a patient and responsive to movement of the patient;
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period; and
a storage, the detector circuit further adapted to store sensor assembly signals in the storage.

17. The patient movement monitoring device of claim 16, wherein the detector circuit is further adapted to convert sensor assembly signals to a digital format before said signal are stored in the storage.

18. The patient movement monitoring device of claim 16, wherein the detector circuit is further adapted to communicate the sensor assembly signals to a personal computer, the personal computer being separate and distinct from the patient movement monitoring device.

19. A patient movement monitoring device comprising:
a sensor assembly adapted to be placed proximal to a patient and responsive to movement of the patient;
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period; and
a second sensor assembly adapted to be placed distal to the patient and responsive to environmental movement in the area of the patient, the second sensor assembly operatively coupled to the detector circuit, the detector circuit further adapted to combine sensor assembly signals and second sensor assembly signals to generate a movement signal representing patient movement substantially void of environmental movement; and use the generated movement signal to determine if a seizure condition exists.

20. The patient movement monitoring device of claim 19, wherein the second sensor assembly is selected from the group consisting of a geophone and fiber optic sensor assemblies.

21. A method to detect a patient seizure comprising:
providing a sensor device on a surface;
receiving a first signal from the sensor device indicating movement of the surface caused by patient movement; and
generating an alarm signal to indicate a patient seizure condition if the first signal indicates at least one of the following conditions: (1) sustained surface movement of more than a first specified magnitude for more than a first specified time period, and (2) a plurality of surface movement episodes of more than a second specified magnitude and more than a second specified duration, the plurality of surface movement episodes occurring within a third specified time period.

22. A method to detect a patient seizure comprising:
receiving a first signal indicating movement of a surface caused by patient movement; and
generating an alarm signal to indicate a patient seizure condition if the first signal indicates at least one of the following conditions: (1) sustained surface movement of more than a first specified magnitude for more than a first specified time period, and (2) a plurality of surface movement episodes of more than a second specified magnitude and more than a second specified duration, the plurality of surface movement episodes occurring within a third specified time period,
wherein the first specified magnitude and the second specified magnitude are substantially the same.

23. The method of claim 22, wherein the third specified time period is longer than the first specified time period and the first specified time period is longer than the second specified time period.

24. A method to detect a patient seizure comprising:
receiving a first signal indicating movement of a surface caused by patient movement;
generating an alarm signal to indicate a patient seizure condition if the first signal indicates at least one of the following conditions: (1) sustained surface movement of more than a first specified magnitude for more than a first specified time period, and (2) a plurality of surface movement episodes of more than a second specified magnitude and more than a second specified duration, the plurality of surface movement episodes occurring within a third specified time period;
receiving a second signal indicating environmental movement;
combining the first and second received signals to generate a movement signal representing patient movement substantially void of environmental movement; and
using the movement signal to indicate the patient seizure condition.

25. A patient movement monitoring device comprising:
a sensor assembly adapted to be placed proximal to a patient and responsive to movement of the patient;
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period; and
a vibration generator activable to test the patient movement monitoring device.

26. The patient movement monitoring device of claim 25, wherein the vibration generator is part of the sensor assembly.

27. The patient movement monitoring device of claim 25, wherein the vibration generator is activated periodically.

28. The patient movement monitoring device of claim 25, wherein the detector circuit monitors for a response from the sensor assembly in response to activation of the vibration generator.

29. The patient movement monitoring device of claim 28, wherein the detector circuit causes generation of a warning alarm if the response is not received.

30. The patient movement monitoring device of claim 25, wherein the vibration generator includes a core-less DC motor member.

31. The method of claim 21, wherein the receiving and generating acts are performed by a monitoring device, the method further comprising generating a test vibration to test the monitoring device.

32. The method of claim 31, wherein generating the test vibration includes activating a vibration generator.

33. The method of claim 31, further comprising indicating a malfunction condition if an expected response is not received in response to the test vibration.

34. A patient movement monitoring device comprising:
a sensor assembly adapted to be placed proximal to a patient and responsive to movement of the patient; and
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period,
wherein the sensor assembly comprises a plurality of geophones.

35. A patient movement monitoring device comprising:
a sensor assembly adapted to be placed proximal to a patient and responsive to movement of the patient;
a detector circuit operatively coupled to the sensor assembly, the detector circuit adapted to generate an alarm signal indicative of a seizure condition if at least one of the following events is detected: (1) sustained patient movement of more than a first specified magnitude for more than a first specified time period, and (2) a plurality of patient movement episodes of more than a second specified magnitude and more than a second specified duration, the plurality of patient movement episodes occurring within a third specified time period; and
a second sensor assembly adapted to detect floor movement, the detector circuit adapted to generate the alarm signal further based on detection of any floor movement.

36. The patient movement monitoring device of claim 35, wherein the detector circuit is adapted to use detection of any floor movement as a reference to determine if the alarm signal is to be generated in response to detection of patient movement.

37. The patient movement monitoring device of claim 5, wherein the sensor assembly comprises at least one of a geophone and a fiber optic device.

38. The method of claim 21, wherein receiving the first signal from the sensor device on the surface comprises receiving the first signal from the sensor device on the surface on which the patient is lying.

39. The method of claim 21, further comprising receiving one or more signals from one or more other sensor devices to detect movement of the surface.

40. An apparatus to detect a seizure condition of a user, comprising:

a sensor device positioned on a surface on which the user is located; and a detector device operatively coupled to the sensor device and adapted to receive an indication from the sensor device representing movement of the surface, the detector device adapted to generate an alarm if the indication corresponds to a seizure condition of the user.

41. The apparatus of claim 40, further comprising at least another sensor device positioned on the surface.

42. The apparatus of claim 41, further comprising at least one reference sensor device positioned at a location to detect any movement of a floor over which the surface sensor devices and detector device are located.

43. The apparatus of claim 40, wherein the sensor device comprises a geophone.

44. The apparatus of claim 40, wherein the sensor device comprises a fiber optic device.

45. The apparatus of claim 40, wherein the sensor device comprises a piezoelectric device.

* * * * *

UNITED STATES PATENT AND TRADEMARK OFFICE
CERTIFICATE OF CORRECTION

PATENT NO. : 6,315,740 B1 Page 1 of 1
APPLICATION NO. : 09/389695
DATED : November 13, 2001
INVENTOR(S) : Balbir Singh It is certified that error appears in the above-identified patent and that said Letters Patent is hereby corrected as shown below:

Column 9:
Line 51, "7" should be --8--; and
Line 65, "12" should be --11--.

Signed and Sealed this

Fifteenth Day of July, 2008

JON W. DUDAS
*Director of the United States Patent and Trademark Office*